rials in amounts given in approximate parts by weight:

| Charge | Parts by Weight (Dry) |
|---|---|
| Vinyl Chloride | 100 |
| Deionized Water | 300 |
| Suspending Agent [1] | 0.5 |
| Initiator A [2] | See Table III |
| Initiator B [3] | See Table III |

[1] Hydroxymethylcellulose
[2] t-Butyl Peroxypivalate
[3] Azobisisobutyronitrile

TABLE III

| Example | 9 | 10 | 11 | Control Samples | | |
| | | | | 12 | 13 | 14 |
|---|---|---|---|---|---|---|
| Initiator A | 0.065 | 0.130 | 0.130 | — | 0.065 | 0.130 |
| Initiator B | 0.065 | 0.033 | 0.065 | 0.065 | — | — |
| Total | 0.130 | 0.163 | 0.195 | 0.065 | 0.065 | 0.130 |
| Percent Yield | 88% | 81% | 98% | 84% | 100% | 99% |

The polymers of Examples 9 – 11 showed a decrease in the amount of torque required to process the polymers over the torques required for the comparable control samples.

The foregoing examples have illustrated the method of the present invention using vinyl chloride as the vinyl halide monomer. Other vinyl halide monomers such as vinyl bromide, vinyl iodide, vinylidene chloride, vinylidene bromide, vinylidene iodide and mixtures thereof can be substituted for the vinyl chloride with equal facility. Vinyl fluoride and vinylidene fluoride which have very low vapor pressures can also be used in high pressure polymerization vessels. As illustrative, 155 parts vinylidene chloride or 90 parts vinyl chloride/15.5 parts vinylidene chloride can be used in place of the 100 parts vinyl chloride with equal facility.

Various copolymers and terpolymers using non-vinyl halide type monomers in combination with the vinyl halide monomer can also be prepared with equal facility. As illustrative, 80 parts vinyl chloride/15.5 parts vinylidene chloride/27.5 parts deithyl fumarate, or 90 parts vinyl chloride/13.75 parts vinyl acetate, or 80 parts vinyl chloride/41.5 parts monomethyl maleate, or 90 parts vinyl chloride/16 parts ethyl acrylate, or 90 parts vinyl chloride/8.5 parts acrylonitrile, or 90 parts vinyl chloride/11.5 parts vinyl ethyl ether can be used in place of the 100 parts vinyl chloride in the preceding examples. Any other non-vinyl halide type monomers such as those listed hereinbefore can be susbstituted with equal facility to prepare copolymers and terpolymers.

The polymers prepared in accordance with the present invention can be used in applications such as the preparation of calendered film, blow molded bottles, extruded flat bed and blown film, extruded articles, tubing, in injection molding, fluidized bed coating, electrostatic powder spraying, rotational casting, additives to other polymers to increase toughness of the resulting blend or wherever polyvinyl chloride is presently used. It is understood that the polymers of the invention can be compounded with additives usually employed in the coating, impregnating and molding composition arts.

Thus, and in accordance with the present invention, there is provided a method for the preparation of a new class of vinyl halide polymers which exhibit improved processing characteristics, without sacrificing physical properties.

We claim:
1. A method for preparing vinyl halide polymers exhibiting improved processing characteristics without sacrificing physical properties comprising:
   a. iniating the free radical suspension polymerization of a ethylenically unsaturated monomer composition containing at least 75%, by weight, of a vinyl halide of the formula:

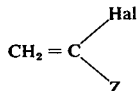

wherein Z is hydrogen or halogen and Hal is halogen at a first reaction temperature; said polymerization being conducted in the presence of a first azo compound as a free radical initiator and of a polymer modifier comprising a polymercaptan chain transfer agent; and, after partial polymerization is accomplished;
   b. changing the reaction temperature to at least one subsequent reaction temperature different from the immediately preceding reaction temperature, adding a second azo compound as a free radical initiator, and continuing said polymerization at said subsequent temperature, said subsequent temperature being conducive to forming a polymer of an average molecular weight different from the average molecular weight obtained during polymerization at said immediately preceding reaction temperature;

one of said azo compounds having a shorter half-life than the other at 80°C.

2. A method as recited in claim 1 wherein said first reaction temperature is higher than said second reaction temperature and said second initiator has a half-life which is shorter than said first at 80° C.

3. A method as recited in claim 1 wherein said monomer composition consists of 100% vinyl chloride.

4. A method as recited in claim 1 wherein said polymerization is initiated at a first reaction temperature which is lower than said second reaction temperature and which is within the range of from about 15° C. to about 50° C. and in the presence of an azo compound having a half-life of less than 30 minutes at 80° C.

5. A method as recited in claim 1 wherein said polymerization at said first reaction temperature is allowed to proceed to from at least 1.0%, by weight, but not more than about 15%, by weight, of the final weight of the polymer composition.

* * * * *

METATHESIS OF CYCLOOLEFINS

This invention is directed to a process for the ring-opening polymerization of unsaturated alicyclic hydrocarbons. It is also directed to novel catalyst systems useful for this ring-opening polymerization process. These catalyst systems are further useful for the interconversion of acyclic olefins according to the method known as the olefin metathesis reaction (also called the olefin dismutation or olefin disproportination reaction) lected from the group consisting of tungsten halides and oxyhalides and molybdenum halides and oxyhalides, (B) at least one compound selected from the group consisting of dialkylaluminum halides, alkylaluminum sesquihalides and alkylaluminum dihalides and (C) at least one hydroxy compound of the general formula ROH wherein R is selected from the group consisting of alkyl and cycloalkyl and wherein R contains a nitrile-substitutent, wherein the molar ratio of A:B:C lies within the range of 1:05–10:0.5–3.

The desired polymerization of alicyclic olefins results amount of the hydroxy compound was added to an 0.5 molar solution of $WCl_6$ in dry benzene and allowed to react for about 24 hours at about 23°C. These solutions were then flushed with dry nitrogen to expel free HCl prior to being used. Ethylaluminum dichloride (EADC) or diethylaluminum chloride (DEAC) were employed as 0.20 molar solutions in benzene.

A series of ring-opening polymerizations were carried out using solutions of freshly-distilled cyclopentene (CP) in benzene. These premix solutions were further purified by being passed through a mixture of silica gel and alumina before being charged to reaction bottles. Polymerizations were conducted with 40 ml. of premix in 4-oz. glass bottles at 0°C. All manipulations of changing premix and catalyst components were conducted under a nitrogen atmosphere. The order of catalyst addition to the polymerization bottles containing premix was tungsten-alcohol component, followed by the organoaluminum component.

In each of the experiments shown in Table 1, 0.40 ml of the solution of the tungsten-alcohol component was employed, which corresponded to a molar ratio of cyclopentene/tungsten of about 5000/1. Polymerizations were terminated with a small amount of isopropanol, and the resultant solutions were dried under vacuum. Inherent viscosities were determined in benzene at 30°C. The percent trans values were determined by a method described in Journal of Polymer Science; Polymer Physics Edition; Volume 11, page 529 (1973) published by John Wiley and Sons, Inc.

Experiments 10 and 11 are comparison tests which show that nitrile-substituted alcohols in which the nitrile is not situated on the carbon adjacent to that bearing the hydroxy group are much less effective as cocatalysts. Experiments 12 and 13 are comparison tests which show that when the nitrile-substituent is not substituted on the hydroxy compound, the effectiveness of the cocatalyst is not significantly increased.

EXAMPLE II

Two polymerizations were carried out in order to illustrate the effectiveness of nitrile-substituted modifiers when very low amounts of catalyst are employed.

A polymerization was carried out similar to Experiment 2 in Example I, except that 0.20 ml of the tungsten catalyst solution was employed instead of 0.40 ml. The molar ratio of CP/W was about 9,200/1. A yield of 73.0 percent was obtained of a strong rubber solid having an inherent viscosity of 4.69.

EXAMPLE III

A polymerization of CP was conducted similar to Experiment 3 of Example I except that the in situ technique was employed to modify the $WCl_6$. Thus, 0.40 ml of an 0.05 molar solution of $WCl_6$ in benzene was introduced into 40 ml of a 20.4 wt-% solution of CP in benzene containing $4 \times 10^{-5}$ moles of 2-hydroxypropanenitrile, followed by 0.40 ml of a 0.20 molar solution of EADC. The yield was 81.2 percent of a rubber polymer having an inherent viscosity of 2.30.

EXAMPLE IV

In the absence of solvent, 25 ml of purified cyclopentene was polymerized at 23°C by the addition of 1.0 ml of a preformed solution of $WCl_6$ and β-hydroxypropanenitrile prepared as described for Experiment 1 in Example I, followed by the addition of 0.60 ml of an 0.20 molar solution of EADC. The reaction was terminated after 120 minutes. A yield of 91.5 percent was obtained of a rubbery solid having an inherent viscosity of 3.24.

While certain representative embodiments and details have been shown for the purpose of illustrating the invention, it will be apparent to those skilled in this art that various changes and modifications may be made therein without departing from the spirit or scope of the invention.

What is claimed is:

1. A cycloolefin metathesis process comprising polymerizing at least one unsaturated alicyclic compound selected from the group consisting of (1) unsaturated alicyclic compounds containing five carbon atoms in the ring and containing one double bond in the ring, (2) nonconjugated unsaturated alicyclic compounds containing at least seven carbon atoms in the ring and at least one double bond in the ring, and (3) polycyclic olefins and diolefins, by subjecting said alicyclic compounds or mixtures thereof to polymerization conditions in the presence of a catalyst system comprising (A) at least one transition metal salt selected from the group consisting of tungsten halides and tungsten oxyhalides, (B) at least one compound selected from the group consisting of alkylaluminum sesquihalides and alkylaluminum dihalides, and (C) at least one hydroxy compound of the general formula ROH wherein R is Table 1

| Exp No. | ROH | Molar Ratio, ROH/$WCl_6$ | EADC, Moles×$10^5$ | DEAC, Moles×$10^5$ | CP conc, wt. % | Polym Time, Min. | Percent Conv. | Inh Visc. | Percent Trans | Appearance |
|---|---|---|---|---|---|---|---|---|---|---|
| 1 | N≡$CCH_2CH_2OH$ | 1 | 6 | — | 18.0 | 60 | 63.0 | 5.47 | 91 | rubbery solid |
| 2 | N≡$CCH_2CH_2OH$ | 2 | 3 | — | 18.0 | 60 | 54.1 | 8.51 | — | " |
| 3 | N≡$CCH_2CH_2OH$ | 2 | 4 | — | 18.0 | 60 | 75.6 | 5.02 | 92 | " |
| 4 | N≡$CCH_2CH_2OH$ | 3 | 8 | — | 18.0 | 60 | 77.0 | 3.51 | — | " |
| 5 | $ClCH_2CH(OH)CH_2C$≡N | 2 | 8 | — | 19.9 | 100 | 76.0 | 3.42 | — | " |
| 6 | [cyclopentane with OH and C≡N]$^b$ | 1 | 8 | — | 19.0 | 120 | 70.3 | — | 86 | " |
| 7 | | 2 | 12 | — | 19.0 | 70 | 53.5 | — | 86 | " |
| 8 | N≡$CCH_2CH_2OH$ | 2 | — | 6 | 19.8 | 60 | 17.3 | 7.60 | — | " |
| 9 | — | 0 | 6 | — | 18.0 | 60 | 1.3 | — | — | — |
| 10 | $(CH_3)_2C(OH)C$≡N | 1 | 6 | — | 21.6 | 90 | 8.9 | — | — | — |
| 11 | N≡$C(CH_2)_6OH$ | 2 | 8 | — | 19.0 | 70 | 13.4 | — | 76 | — |
| 12 | $CH_3CH_2OH$ | 2 | 8 | — | 21.1 | 120 | 19.9 | — | — | — |
| 13$^a$ | $CH_3CH_2OH$ | 2 | 6 | — | 17.7 | 60 | 17.7 | — | — | — |

$^a$$CH_3C$≡N was added to the $WCl_6$ solution with the $CH_3CH_2OH$ during the preforming step; molar ratio $CH_3C$≡N/$WCl_6$ = 2/1.
$^b$2-hydroxycyclopentanenitrile used in 6 and 7.

selected from the group consisting of alkyl and cycloalkyl and wherein R contains a nitrile substituent, wherein the molar ratio of A:B:C lies within the range of 1:0.5–10:0.5–3.

2. A process of claim 1 wherein R contains a nitrile substituent situated on the carbon atom adjacent to that bearing the hydroxy group.

3. A process according to claim 1 wherein (A) is selected from the group consisting of $WCl_6$, $WBr_6$ and $WOCl_4$.

4. A process according to claim 1 wherein (C) is 2-hydroxypropionitrile or 2-hydroxy-1-methylpropionitrile.

5. A process according to claim 2 wherein (A) is selected from the group consisting of $WCl_6$, $WBr_6$ and $WOCl_4$ and (C) is 2-hydroxypropionitrile or 2-hydroxy-1-methylpropionitrile.

6. A process according to claim 1 wherein cyclopentene is polymerized.

7. A process according to claim 5 wherein cyclopentene is polymerized.

8. The method according to claim 7 in which (A) is $WCl_6$.

* * * * *